United States Patent [19]
Hudnall

[11] Patent Number: 5,608,120
[45] Date of Patent: Mar. 4, 1997

[54] PROCESS FOR THE PREPARATION OF (ARYLETHYL)-HYDROQUINONES AND DIESTERS THEREOF

[75] Inventor: Phillip M. Hudnall, Kingsport, Tenn.

[73] Assignee: Granmont, Inc., Tucson, Ariz.

[21] Appl. No.: 390,932

[22] Filed: Feb. 17, 1995

Related U.S. Application Data

[63] Continuation of Ser. No. 723,708, Jun. 24, 1991, abandoned, which is a continuation of Ser. No. 200,490, May 31, 1988, abandoned.

[51] Int. Cl.$^6$ .................................................. C07C 39/14
[52] U.S. Cl. .............................................................. 568/744
[58] Field of Search ........................... 568/744; 560/138, 560/140

[56] References Cited

U.S. PATENT DOCUMENTS

| | | | |
|---|---|---|---|
| 2,714,120 | 7/1955 | Kehe | 568/744 |
| 2,793,239 | 5/1957 | Toland | 568/744 |
| 4,661,645 | 4/1987 | Lee et al. | 568/744 |
| 5,043,483 | 8/1991 | Sogli et al. | 568/744 |

FOREIGN PATENT DOCUMENTS

| | | | |
|---|---|---|---|
| 0319310 | 6/1989 | European Pat. Off. . | |
| 0347835 | 12/1989 | European Pat. Off. . | |
| 57-188535 | 11/1982 | Japan . | |
| 58-140035 | 8/1983 | Japan . | |
| 140035 | 8/1983 | Japan | 568/744 |
| 228694 | 10/1968 | U.S.S.R. . | |
| 330151 | 10/1972 | U.S.S.R. . | |
| 929622 | 5/1982 | U.S.S.R. . | |
| WO89/120937 | 12/1989 | WIPO . | |

OTHER PUBLICATIONS

*Hackh's Chemical Dictionary*, p. 648 (entry concerning sulfuric acid) (4th edition 1969).
*Kirk–Othmer Encyclopedia of Chemical Technology*, vol. 22, pp. 192–197 (part of entry concerning sulfuric acid) (3rd edition 1983).
Buu–Hoi et al., "Condensation of Phenols and Naphthols with Styrene," *J. Org. Chem.*, vol. 17, pp. 243–248 (1952).
Weygard et al., *Preparative Organic Chemistry*, John Wiley & Sons, New York, p. 374 (1972).
*Hackh's Chemical Dictionary*, p. 515 (entry concerning phosphoric acid) (4th edition 1969).
*The Merck Index*, pp. 7315 and 7323 (11th edition 1989).
Weygand et al, Preparation Organic Chemistry John Wiley & Sons, N.Y., 1972, p. 374.

*Primary Examiner*—Samuel Barts
*Attorney, Agent, or Firm*—Bryan Cave LLP

[57] ABSTRACT

Disclosed is a process for the preparation of 2-(1-arylethyl) hydroquinones by the reaction of a hydroquinone compound with an arylvinyl compound in the presence of a phosphoric acid alkylation catalyst in a two-phase liquid reaction medium comprising water and a water-immiscible organic solvent. Formation of the corresponding bis-(1-arylethyl)hydroquinone is minimized resulting in excellent selectivity to the mono-(1-arylethyl)hydroquinone compound.

12 Claims, No Drawings

PROCESS FOR THE PREPARATION OF (ARYLETHYL)-HYDROQUINONES AND DIESTERS THEREOF

This is a continuation of U.S. application Ser. No. 07/723,708, filed Jun. 24, 1991, now abandoned which is a continuation of U.S. application Ser. No. 07/200,490, filed May 31, 1988 (now abandoned).

This invention concerns a novel process for the preparation of 2-(1-arylethyl)hydroquinones and diesters thereof wherein formation of bis-(1-arylethyl)hydroquinones is suppressed. More particularly, this invention concerns the preparation of 2-(1-arylethyl)hydroquinones by the reaction of a hydroquinone compound with an arylvinyl compound in the presence of a phosphoric acid alkylation catalyst in a two-phase, liquid organic/aqueous reaction system.

The reaction of phenols and hydroquinones with arylvinyl compounds is well known. U.S. Pat. No. 2,432,356 discloses the preparation of substituted phenols by the reaction of phenol with styrene in the presence of sulfuric acid. The dialkylation of a dihydric phenol with an arylvinyl compound in the presence of an acidic catalyst is described in U.S. Pat. No. 2,506,410. More recently, the preparation of 2-(1-phenylethyl)hydroquinone (PEHQ) in a yield of 58% by the reaction of hydroquinone with alphamethylbenzyl alcohol at 140° C. in the presence of phosphoric acid has been reported by Yusupov et al., Deposited Doc., VINITI 325-76, 1976 (C.A.88:89256a). Japanese Kokai 59/112935 discloses the reequilibration of 2,5-bis(alpha-methylbenzyl)hydroquinone in a mixture of hydroquinone and styrene over 100% phosphoric acid at 135° C., giving 91% of the monosubstituted compound (PEHQ).

U.S., Pat. Nos. 4,600,765 and 4,661,645 describe the preparation of PEHQ by the reaction of hydroquinone and styrene in a polyether solvent at 140° C. using p-toluenesulfonic acid as the catalyst. A ratio of mono-substituted product (PEHQ) to di-substituted product of 2.3:1 was obtained at a hydroquinone conversion of 75%, employing a stoichiometry of 0.88 moles of styrene per mole of hydroquinone. The overall yield of PEHQ, which was isolated by fractional vacuum distillation, was 58.3% and the yield from consumed hydroquinone was 77.3%.

A more recent patent, U.S. Pat. No. 4,734,531, discloses the synthesis of (1-phenylethyl)hydroquinone by the reaction of styrene and hydroquinone in the presence of a zeolite molecular seive.

It has been discovered that a hydroquinone compound and an arylvinyl compound such as styrene may be reacted in approximately equimolar amounts in the presence of phosphoric acid and a liquid, two-phase solvent system to obtain the desired mono-substituted compound in excellent yields and remarkable selectivity. The selectivity of this novel process gives ratios of the desired monosubstituted compound to the undesired di-substituted compound of at least 12:1 and typically in excess of 18:1 at near quantitative conversion of the hydroquinone compound.

Thus, the process provided by this invention comprises the preparation of a mono-(1-arylethyl)hydroquinone compound by reacting a hydroquinone compound with an arylvinyl compound in the presence of a catalytically-effective amount of phosphoric acid in a two-phase, liquid reaction medium comprising water and a hydrocarbon solvent. The mono-(1-arylethyl)hydroquinone may be used as stabilizers or inhibitors in various organic substances subject to oxidative degradation, e.g., vegetable oils, or as monomers in the preparation of high performance polyesters such as those described in U.S. Pat. No. 4,600,765.

The hydroquinone compounds which may be used in the process include unsubstituted hydroquinone or hydroquinone substituted, for example, with alkyl such as alkyl of up to 12 carbon atoms, e.g., methyl, ethyl, propyl, butyl, 1,1-dimethylethyl, 1,1-dimethylethyl, hexyl, 2-ethylhexyl, 1,1,3,3-tetramethylbutyl, etc. or halogen, e.g., chloro. The most preferred hydroquinone compound reactant is unsubstituted hydroquinone. Although the arylvinyl reactant most commonly is styrene, arylvinyl compounds in which the aryl moiety is substituted with alkyl such as the alkyl groups described above, alkoxy of up to 12 carbon atoms, halogen, etc. may be used. The substituted hydroquinone and styrene reactants preferably do not bear more than one substituent.

Examples of the hydrocarbon solvents which may be used in the novel process provided by this invention include aromatic and aliphatic hydrocarbons and mixtures of such hydrocarbons with other solvents such as ketones having at least 6 carbon atoms such as 4-methyl-2-pentanone, 5-methyl-2-hexanone, etc. Suitable aromatic and altphatic hydrocarbon solvents include those having about 6 to 12 carbon atoms such as benzene, toluene, the xylenes, heptane, etc. The amount of the organic phase, i.e., the organic solvent, is not critical to the operation of the process and can vary substantially depending on various factors such as the equipment used, the mode of operation and the like. While weight ratios of organic solvent to hydroquinone reactant in the range of about 30 to 0.1 may be used, weight ratios in the range about 3 to 4 normally will be used. The amount of water present may be in the range of about 10 to 200 weight percent based on the weight of the hydroquinone reactant, preferably in the range of 50 to 100 which is a compromise of mass transfer and throughput factors. Also, the amount of water employed normally will be in the range of about 10 to 50, preferably about 10 to 20, weight percent based on the weight of the phosphoric acid.

The amount of phosphoric acid catalyst, i.e., 100 percent phosphoric acid, typically is in the range of about 5 to 600 weight percent based on the weight of the organic solvent. Preferably, the amount of catalyst present is about 20 to 150 weight percent (same basis), most preferably, about 80 to 120 weight percent.

The hydroquinone alkylation conditions of temperature and pressure are not critical to the successful operation of the process so long as a liquid phase reaction system is maintained. The reaction temperature typically will be in the range of about 60° to 200° C. with the range of about 85° to 110° C. being preferred. The pressure within the reaction vessel is not important and thus pressures slightly below or above atmospheric may be used. The reaction pressure preferably is atmospheric.

Upon the completion of the reaction, the product may be recovered directly from the resulting reaction mixture by first removing the lower, catalyst-containing, aqueous phase which may be utilized as the catalyst/aqueous phase in the synthesis of additional product. The product-containing, organic phase may then be washed with water to remove traces of acid and stripped of solvent according to known techniques and the product residue may be used as is if end-use requirements permit. The crude product may be further purified, if necessary, by vacuum distillation.

Alternatively, the (1-arylethyl)hydroquinone product may be recovered as its di-alkanoate ester by reacting the solvent-stripped product with an anhydride of a carboxylic acid of 2 to 4 carbon atoms, especially acetic anhydride, to convert the product to the corresponding (1-arylethyl)hydroquinone dialkanoate which can be separated from the bis-(1-arylethyl)hydroquinone dialkanoate by distillation. In contrast to PEHQ which distills at 200° C. vapor temperature at 0.6 mm pressure, the distillation conditions for PEHQ diacetate are less severe: 195° C. vapor temperature at 4 mm pressure. The milder distillation conditions of this additional embodiment of the invention permit the use of general purpose distillation equipment, provides a product which is a mobile liquid at room temperature and provides a grade of product which is suitable for many end uses such as polymer preparation.

The (1-arylethyl)hydroquinone dialkanoates, which are believed to be novel compounds, may be used advantageously in the preparation of polyesters. The diester compounds can be polymerized with terephthalic acid or dimethyl terephthalate to produce high molecular weight, linear polyesters. In contrast, the preparation of polyesters from the unesterified (1-arylethyl)hydroquinone compounds according to U.S. Pat. No. 4,600,765 requires the use of terephthaloyl chloride, a polymer intermediate not commonly used in the manufacture of polyesters.

The process of the present invention may be practiced in a batch, semi-continuous or continuous manner. In batch operation, the phosphoric acid catalyst, water (typically in admixture with the catalyst), the hyroquinone compound reactant and water-immiscible organic solvent are added to a suitable reaction vessel, e.g., a reactor equipped with an agitator and means for removing the aqueous phase and stripping off the organic solvent at the completion of the reaction. The reaction mixture is heated to the desired reaction temperature, the arylvinyl reactant is added and the resulting reaction mixture is agitated at the reaction temperature selected until a predetermined amount of one or both of the reactants has been consumed, e.g., by analysis of a sample taken from the reactor. The arylvinyl compound may be added, continuously or intermittently, over a period of time to avoid or minimize the polymerization thereof. The product may be isolated, either as the hydroquinone compound or its diester, and, optionally, purified according to conventional procedures such as those described above.

In continuous operation, hydroquinone reactant and arylvinyl reactant are continuously fed, along with recycle organic solvent, to an agitated reactor containing unreacted hydroquinone compound and the catalyst and in which the reaction mixture is maintained at an appropriate reaction temperature and pressure. The organic phase of the reaction mixture is continuously removed from the reactor and fed to a work-up system wherein the organic phase is water-washed and subsequently stripped of hydrocarbon solvent. The stripped, crude product then may be purified if necessary or converted to its diester as described above and processed further.

The novel process is further illustrated by the following examples.

EXAMPLE 1

To a stirred, three-neck 500 mL flask equipped with a thermometer, means for adding styrene and a bottom outlet valve are charged 100.0 g of a mixture consisting of 85 weight percent phosphoric acid and 15 weight percent water, 27.5 g (0.25 mol) of hydroquinone and 100 mL toluene. The mixture is heated to 100° C. and 26.0 g (0.25 mol) styrene are added dropwise at 98°–102° C. over three hours. The reaction mixture then is agitated at 98°–102° C. for an additional five hours, agitation is stopped, the phases are allowed to separate and the bottom phosphoric acid-containing phase is decanted and held for recycle. The upper toluene phase containing the product is washed twice with 200 mL of water at 90° C. and thereafter the toluene is removed by stripping the organic phase up to a pot temperature of 150° C. The product weighed 52.1 g, a 97.3 weight percent yield. Gas chromatography analysis of the product showed that it contained (by area percent) 92.7% 2-(1-phenylethyl)hydroquinone (PEHQ) and 5.1% dialkylated compounds. The selectivity, described as the ratio of PEHQ to dialkylated compounds, is 18.2:1 and an overall weight yield of hydroquinone to PEHQ of 90.2%.

EXAMPLE 2

The procedure of Example 1 is repeated using 54.5 g of a mixture consisting of 85 weight percent phosphoric acid and 15 weight percent water, 36.4 g (0.33 mol) hydroquinone, 60 mL xylene, 60 mL 5-methyl-2-hexanone and 22.9 g (0.22 mol) styrene. The crude product obtained contained 94.4 percent PEHQ and 3.5 percent dialkylated compounds, giving a selectivity ratio of 27.0:1.

COMPARATIVE EXAMPLE 1

The procedure of Example 1 is repeated except that no hydrocarbon solvent was used and the water was removed by azeotropic drying of the mixture prior to the addition of the styrene. The product obtained weighed 51.3 g and contained 71.7 percent PEHQ and 27.9 percent dtalkylated compounds which is a PEHQ:dialkylated compounds ratio of 2.6:1. The overall yield of hydroquinone to PEHQ is 68.7%.

COMPARATIVE EXAMPLE 2

Example 2 is repeated except that the water added with the phosphoric acid was removed by azeotropic distillation prior to the addition of the styrene. The product obtained contained 60.9 percent PEHQ and 24.7 percent dialkylated compounds giving a selectivity ratio of 2.5:1.

EXAMPLE 3

To a three-neck, one-liter flask are charged 208.0 g (189.1 g, 100% basis, 0.88 mol) of crude, stripped PEHQ and 100 g acetic acid. The reaction mixture is heated to 90° C. and 225.0 g (2.2 mol) of acetic anhydride is added over 15 minutes. After heating at reflux for 4 hours, the reaction mixture is stripped of acetic acid and unreacted acetic anhydride at 100 mm pressure up to a pot temperature of 195° C. At this point, the diacetylated product may be cooled and isolated or further refined by distillation. The PEHQ diacetate is this example is distilled through a 10-inch column filled with Penn State packing. The product (237.5 g) is isolated as a pale yellow oil. Analysis of the product confirmed the product assay to be 98.2% PEHQ diacetate, providing a yield of 88.8% from crude PEHQ.

EXAMPLE 4

To a stirred, three-neck 1 liter flask equipped with a thermometer, means for adding styrene and a bottom outlet valve are charged 200.0 g of 85% phosphoric acid (containing 15 weight percent water), 83.0 g water, 55.06 g (0.5 mol) hydroquinone and 150.0 g toluene. The contents of the flask are heated to 100° C. and 52.1 g (0.5 mol) styrene are added dropwise at about 100° C. over a period of about five hours. The reaction mixture is then agitated at about 100° C. for a total of 12 hours. The two phases of the reaction medium are then allowed to separate and the lower, aqueous phase is drained from the flask. The remaining toluene phase is washed four times with 200 mL portions of water (until the wash water has a pH of 5.0 of less). Toluene is then removed to a pot temperature of 160° C. Gas chromatography analysis of the product showed that it contained 89.3 g of PEHQ, 83.4% of theory.

The invention has been described in detail with particular reference to preferred embodiments thereof, but it will be understood that variations and modifications can be effected within the and spirit scope of the invention.

We claim:

1. Process for the preparation of a mono-(1-arylethyl)-hydroquinone compound which comprises reacting a hydroquinone compound with an arylvinyl compound in the presence of a catalytically effective amount of phosphoric acid in a two-phase, liquid reaction medium comprising water and a water-immiscible hydrocarbon solvent, wherein the aryl moiety is phenyl or phenyl substituted with alkyl of up to 12 carbon atoms, alkoxy of up to 12 carbon atoms or halogen.

2. Process according to claim 1 wherein the weight ratio of organic solvent to hydroquinone compound thereof is about 30 to 0.1 and the amount of water present is about 10 to 200 weight percent based on the weight of the hydroquinone reactant.

3. Process according to claim 2 wherein the amount of phosphoric acid present is about 20 to 150 weight percent based on the weight of the water-immiscible hydrocarbon solvent, the amount of water present is about 10 to 50 weight percent based on the phosphoric acid and the reaction is carried out at a temperature in the range of 85° to 110° C.

4. Process for the preparation of mono-(1-phenylethyl) hydroquinone which comprises reacting hydroquinone and styrene at a temperature of about 85° to 110° C. in the presence of a catalytically-effective amount of phosphoric acid in a two phase, liquid reaction medium comprising water and a hydrocarbon solvent.

5. Process according to claim 4 wherein the hydrocarbon solvent is toluene, xylene or a mixture thereof present in a weight ratio based on the hydroquinone of about 3 to 4, the amount of phosphoric acid present is about 80 to 120 weight percent based on the weight of the organic solvent and the amount of water present is about 10 to 20 weight percent based on the weight of the phosphoric acid.

6. Process for the preparation of mono-(1-phenylethyl) hydroquinone diacetate which comprises the steps of:
   (1) reacting hydroquinone with styrene in the presence of a catalytically-effective amount of phosphoric acid and a two-phase, liquid reaction medium comprising water and a hydrocarbon solvent;
   (2) separating the phosphoric acid-containing aqueous phase from the product-containing hydrocarbon phase; and
   (3) removing hydrocarbon solvent from the hydrocarbon phase and contacting the residue-product with acetic anhydride.

7. A process for the arylethylation of hydroquinone, comprising reacting hydroquinone with an arylvinyl compound, wherein the aryl is selected from the group consisting of phenyl and phenyl substituted with alkyl of up to 12 carbon atoms, alkoxy of up to 12 carbon atoms or halogen, in the presence of an organic solvent selected from the group consisting of toluene, xylenes and mixtures thereof and in the presence of a catalyst consisting essentially of phosphoric acid diluted in water to 80–90%.

8. A process according to claim 7, wherein the arylvinyl compound is styrene.

9. A process according to claim 7, wherein the molar ratio of hydroquinone/arylvinyl compound is within the range 1.5 to 1.

10. A process according to claim 7, wherein the weight ratio of the solvent to the hydroquinone is within the range of from about 30 to 0.5.

11. A process for the arylethylation of hydroquinone, comprising reacting hydroquinone with an arylvinyl compound, wherein the aryl is selected from the group consisting of phenyl and phenyl substituted with alkyl of up to 12 carbon atoms, alkoxy of up to 12 carbon atoms or halogen, in the presence of an organic solvent selected from the group consisting of toluene, xylenes and mixtures thereof and in the presence of a catalyst consisting essentially of phosphoric acid diluted in water to 50–90%.

12. A process according to claim 7, wherein the reaction temperature is within the range of 85° to 110° C.

* * * * *